(12) United States Patent
Ukil et al.

(10) Patent No.: US 9,978,392 B2
(45) Date of Patent: May 22, 2018

(54) NOISY SIGNAL IDENTIFICATION FROM NON-STATIONARY AUDIO SIGNALS

(71) Applicant: Tata Consultancy Services Limited, Mumbai (IN)

(72) Inventors: Arijit Ukil, Kolkata (IN); Soma Bandyopadhyay, Kolkata (IN); Chetanya Puri, Kolkata (IN); Arpan Pal, Kolkata (IN); Rituraj Singh, Kolkata (IN); Ayan Mukherjee, Kolkata (IN); Debayan Mukherjee, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days. days.

(21) Appl. No.: 15/456,172

(22) Filed: Mar. 10, 2017

(65) Prior Publication Data
US 2018/0075861 A1    Mar. 15, 2018

(30) Foreign Application Priority Data

Sep. 9, 2016    (IN) .............................. 201621030833

(51) Int. Cl.
*G10L 25/84* (2013.01)
*G10L 25/78* (2013.01)
(Continued)

(52) U.S. Cl.
CPC .......... *G10L 21/0232* (2013.01); *G10L 15/02* (2013.01); *G10L 15/063* (2013.01);
(Continued)

(58) Field of Classification Search
CPC ............... G10L 25/78; G10L 2025/783; G10L 2025/786; G10L 25/81; G10L 25/84;
(Continued)

(56) References Cited

U.S. PATENT DOCUMENTS 4,696,041 A * 9/1987 Sakata ................. G10L 25/87
                                              704/233
4,982,341 A * 1/1991 Laurent ................. G10L 25/78
                                              704/250
(Continued)

FOREIGN PATENT DOCUMENTS

CN           105326482 A         2/2016

OTHER PUBLICATIONS

Laverty, "Detection of Nonstationary Noise and Improved Voice Activity Detection in an Automotive Hands-free Environment", Worcester Polytechnic Institute, 96 pages, (2005) http://spinlab.wpi.edu/pubs/Laverty_THESIS_2005.pdf.
(Continued)

*Primary Examiner* — Eric Yen
(74) *Attorney, Agent, or Firm* — Finnegan, Henderson, Farabow, Garrett & Dunner LLP

(57) ABSTRACT

Traditionally known classification methods of non-stationary physiological audio signals as noisy and clean involve human intervention, may involve dependency on particular type of classifier and further analyses is carried out on classified clean signals. However, in non-stationary audio signals a major portion may end up being classified as noisy and hence may get rejected which may cause missing of intelligence which could have been derived from lightly noisy audio signals that may be critical. The present disclosure enables automation of classification based on auto-thresholding and statistical isolation wherein noisy signals are further classified as highly noisy and lightly noisy through continuous dynamic learning.

17 Claims, 4 Drawing Sheets

(51) Int. Cl.
  *G10L 25/93* (2013.01)
  *G10L 21/0232* (2013.01)
  *G10L 15/06* (2013.01)
  *G10L 15/02* (2006.01)

(52) U.S. Cl.
  CPC ........ *G10L 25/84* (2013.01); *G10L 2025/786* (2013.01); *G10L 2025/935* (2013.01)

(58) Field of Classification Search
  CPC ... G10L 25/87; G10L 25/93; G10L 2025/932; G10L 2025/935; G10L 2025/937
  See application file for complete search history.

(56) References Cited

U.S. PATENT DOCUMENTS

| | | | | |
|---|---|---|---|---|
| 5,216,747 | A * | 6/1993 | Hardwick | G10L 19/087 704/207 |
| 5,263,097 | A * | 11/1993 | Katz | G01S 3/7865 382/190 |
| 5,373,460 | A * | 12/1994 | Marks, II | G06F 17/141 704/E11.002 |
| 5,611,019 | A * | 3/1997 | Nakatoh | G10L 15/063 704/233 |
| 5,649,055 | A * | 7/1997 | Gupta | G10L 25/78 704/208 |
| 6,182,035 | B1 * | 1/2001 | Mekuria | G10L 25/78 704/230 |
| 6,453,291 | B1 * | 9/2002 | Ashley | G10L 25/78 704/200 |
| 6,636,829 | B1 * | 10/2003 | Benyassine | G10L 19/005 704/201 |
| 6,898,566 | B1 * | 5/2005 | Benyassine | G10L 19/22 704/207 |
| 8,731,917 | B2 * | 5/2014 | Grancharov | G10L 19/26 704/200.1 |
| 8,949,077 | B2 | 2/2015 | Fu et al. | |
| 9,378,746 | B2 * | 6/2016 | Choo | G10L 19/008 |
| 9,685,193 | B2 * | 6/2017 | Cunico | G11B 27/036 |
| 2002/0103643 | A1 * | 8/2002 | Rotola-Pukkila | G10L 19/012 704/233 |
| 2002/0143528 | A1 * | 10/2002 | Deligne | G10L 15/20 704/224 |
| 2003/0055535 | A1 * | 3/2003 | Voeller | G10L 15/26 700/279 |
| 2003/0078770 | A1 * | 4/2003 | Fischer | G10L 25/78 704/214 |
| 2003/0144840 | A1 * | 7/2003 | Ma | G10L 25/78 704/249 |
| 2004/0006737 | A1 * | 1/2004 | Colbath | G10L 25/78 715/201 |
| 2006/0098809 | A1 * | 5/2006 | Nongpiur | G10L 21/0364 379/406.14 |
| 2007/0118364 | A1 * | 5/2007 | Wise | G10L 25/78 704/215 |
| 2009/0154726 | A1 * | 6/2009 | Taenzer | G10L 25/78 381/94.1 |
| 2009/0271187 | A1 * | 10/2009 | Yen | G10L 21/0208 704/226 |
| 2010/0088094 | A1 * | 4/2010 | Wang | G10L 25/78 704/233 |
| 2011/0035213 | A1 * | 2/2011 | Malenovsky | G10L 25/78 704/208 |
| 2012/0016249 | A1 | 1/2012 | Lian et al. | |
| 2015/0269933 | A1 * | 9/2015 | Yu | G10L 15/16 704/232 |
| 2016/0099007 | A1 * | 4/2016 | Alvarez | G10L 21/034 704/225 |
| 2016/0260429 | A1 * | 9/2016 | Jin | G10L 15/08 |
| 2017/0169828 | A1 * | 6/2017 | Sachdev | G10L 17/04 |

OTHER PUBLICATIONS

Nunes, "Identification and Removal of Noise in Cardiac Signals", University of Coimbra, 97 pages, (2016) https://estudogeral.sib.uc.pt/bitstream/10316/31240/1/Identification%20and%20Removal%20of%20Noise%20in%-20Cardiac%20Signals.pd.

Kumar et al., "Noise detection during heart sound recording using periodicity signatures", Physiological Measurement, IOPscience, vol. 32, No. 5, 21 pages, (2011) https://eden.dei.uc.pt/~ruipedro/publications/Journals/Phys%20Meas%202011.pdf.

* cited by examiner

NOISY SIGNAL IDENTIFICATION FROM NON-STATIONARY AUDIO SIGNALS

PRIORITY CLAIM

This U.S. patent application claims priority under 35 U.S.C. § 119 to: India Application No. 201621030833 filed on Sep. 9, 2016. The entire contents of the aforementioned application are incorporated herein by reference.

TECHNICAL FIELD

The embodiments herein generally relate to noisy signal identification from non-stationary audio signals, and more particularly to systems and methods for automating the noisy signal identification with the ability to perform finer classification of lightly noisy audio signals from the noisy audio signals.

BACKGROUND

Non-stationary physiological audio signals like phonocardiogram (PCG) often contain sufficient noisy components that cause further decision making and analyses highly error-prone. Detection or identification of noisy non-stationary physiological audio signals through automated methods would imply that further analysis is done only on clean non-stationary physiological audio signal. For instance, automated classification of pathology in heart sound recordings has been performed for over 50 years, but still presents challenges. Current studies for heart sound classification are flawed because they predominantly validate only clean recordings. However, in practice PCG recordings have poor signal quality and often there exists high amount of noise. It is thus imperative to further extract a lightly noisy component of the recordings from the otherwise rejected noisy component to ensure that critical information in the lightly noisy components are not missed out during further analyses.

SUMMARY

Embodiments of the present disclosure present technological improvements as solutions to one or more of the above-mentioned technical problems recognized by the inventors in conventional systems.

In an aspect, there is provided a processor implemented method comprising: receiving a feature set (F) of a plurality of features associated with non-stationary audio signals; receiving a training set comprising a plurality of non-stationary clean audio signals (C) and non-stationary noisy audio signals (N); generating a unique and distinctive feature set (UF) based on the training set and the feature set (F); dynamically generating an unbiased threshold of unique feature attribute value (UFAV) and polarity (P) associated with each of the unique and distinctive features of the unique and distinctive feature set (UF); identifying a test signal as non-stationary noisy test signal or non-stationary clean test signal by statistical isolation based on (i) the unique feature attribute value (UFAV) and the polarity (P) associated with each of the unique and distinctive features of the test signal and (ii) the dynamically generated unbiased threshold of the unique feature attribute value (UFAV) and the polarity (P); and classifying the non-stationary noisy test signal further as one of lightly noisy test signal and highly noisy test signal based on one or more pre-defined conditions.

In another aspect, there is provided a system comprising: one or more data storage devices operatively coupled to the one or more processors and configured to store instructions configured for execution by the one or more processors to: receive a feature set (F) of a plurality of features associated with non-stationary audio signals; receive a training set comprising a plurality of non-stationary clean audio signals (C) and non-stationary noisy audio signals (N); generate a unique and distinctive feature set (UF) based on the training set and the feature set; dynamically generate an unbiased threshold of unique feature attribute value (UFAV) and polarity (P) associated with each of the unique and distinctive features of the unique and distinctive feature set (UF); identify a test signal as non-stationary noisy test signal or non-stationary clean test signal by statistical isolation based on (i) the unique feature attribute value (UFAV) and the polarity (P) associated with each of the unique and distinctive features of the test signal and (ii) the dynamically generated unbiased threshold of the unique feature attribute value (UFAV) and the polarity (P); and classify the non-stationary noisy test signal further as one of lightly noisy test signal and highly noisy test signal based on one or more pre-defined conditions.

In yet another aspect, there is provided a computer program product comprising a non-transitory computer readable medium having a computer readable program embodied therein, wherein the computer readable program, when executed on a computing device, causes the computing device to: receive a feature set (F) of a plurality of features associated with non-stationary audio signals; receive a training set comprising a plurality of non-stationary clean audio signals (C) and non-stationary noisy audio signals (N); generate a unique and distinctive feature set (UF) based on the training set and the feature set; dynamically generate an unbiased threshold of unique feature attribute value (UFAV) and polarity (P) associated with each of the unique and distinctive features of the unique and distinctive feature set (UF); identify a test signal as non-stationary noisy test signal or non-stationary clean test signal by statistical isolation based on (i) the unique feature attribute value (UFAV) and the polarity (P) associated with each of the unique and distinctive features of the test signal and (ii) the dynamically generated unbiased threshold of the unique feature attribute value (UFAV) and the polarity (P); and classify the non-stationary noisy test signal further as one of lightly noisy test signal and highly noisy test signal based on one or more pre-defined conditions.

In an embodiment of the present disclosure, the one or more hardware processors are further configured to generate one or more of: to generate the unique and distinctive feature set (UF) by: extracting feature values for each of the plurality of features associated with the plurality of non-stationary clean audio signals (C) and the non-stationary noisy audio signals (N); and classifying each feature from the feature set as a unique distinctive feature of a unique distinctive feature set (UF) if one condition of: (i) minimum feature value associated with the non-stationary clean audio signal (C) is greater than maximum feature value associated with the non-stationary noisy audio signal (N) by a first pre-determined percentage of the plurality of the non-stationary clean audio signals (C) and a second pre-determined percentage of the plurality of the non-stationary noisy audio signals (N); and (ii) minimum feature value associated with the non-stationary noisy audio signal (N) is greater than maximum feature value associated with the non-stationary clean audio signal (C) by at least the first pre-determined percentage of the plurality of the plurality of non-stationary clean audio signals (C) and the second percentage of the plurality of the non-stationary noisy audio signals (N), is satisfied.

In an embodiment of the present disclosure, the first pre-determined percentage and the second pre-determined percentage is 90%.

In an embodiment of the present disclosure, the unique feature attribute value (UFAV) is mean of (i) median of values associated with unique and distinctive features of the plurality of non-stationary clean audio signals and (ii) median of values associated with the unique and distinctive features of the non-stationary noisy audio signals.

In an embodiment of the present disclosure, the one or more hardware processors are further configured to identify the test signal as non-stationary noisy test signal or non-stationary clean test signal if one condition of: bucketing the unique and distinctive features of the test signal into clean bucket ($B_C$) and noisy bucket ($B_N$) based on a strict majority voting rule on cardinality of the clean bucket ($B_C$) and cardinality of the noisy bucket ($B_N$); and bucketing the unique and distinctive features of the test signal into clean bucket ($B_C$) and noisy bucket ($B_N$) based on a weighted majority voting rule on cardinality of the clean bucket ($B_C$) and cardinality of the noisy bucket ($B_N$); is satisfied.

In an embodiment of the present disclosure, the one or more hardware processors are further configured to classify the non-stationary noisy test signal further as lightly noisy test signal if one condition from the one or more pre-defined conditions: cardinality of the clean bucket ($B_C$) is greater than the cardinality of the unique and distinctive feature set (UF) by a first pre-determined value; and Euclidian distance between the unique feature attribute value (UFAV) and the values associated with unique and distinctive features of the noisy signal is lesser than the unique feature attribute value (UFAV) by a second pre-determined value in at least a part of the cardinality of the unique and distinctive feature set (UF); is satisfied. In an embodiment, the cardinality of the clean bucket ($B_C$) is not less than one third of the cardinality of the unique and distinctive feature set (UF). In an embodiment, the Euclidian distance between the unique feature attribute value (UFAV) and the values associated with unique and distinctive features of the noisy signal is not greater than 10% of the unique feature attribute value (UFAV) in at least 50% of the cardinality of the unique and distinctive feature set (UF).

It is to be understood that both the foregoing general description and the following detailed description are exemplary and explanatory only and are not restrictive of the embodiments of the present disclosure, as claimed.

BRIEF DESCRIPTION OF THE DRAWINGS

The embodiments herein will be better understood from the following detailed description with reference to the drawings, in which.

Figure 1:
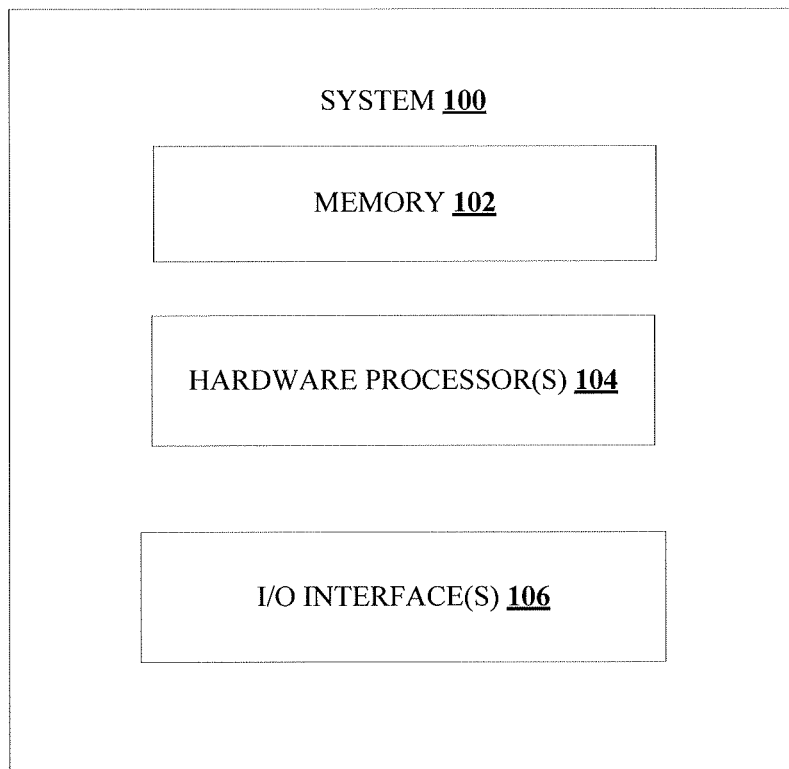
FIG. 1 illustrates an exemplary block diagram of a system for noisy signal identification from non-stationary audio signals, in accordance with an embodiment of the present disclosure.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Before setting forth the detailed explanation, it is noted that all of the discussion below, regardless of the particular implementation being described, is exemplary in nature, rather than limiting.

Systems and methods of the present disclosure aim to identify noisy signal form non-stationary audio signals and further classify them into lightly noisy and highly noisy non-stationary audio signals. This ensures that critical information that may be contained in the lightly noisy non-stationary audio signals is not lost when the noisy signal is rejected for further processing. In an embodiment, such non-stationary audio signals may be physiological signals such as phonocardiogram (PCG).

Referring now to the drawings, and more particularly to FIGS. 1 through 4, where similar reference characters denote corresponding features consistently throughout the figures, there are shown preferred embodiments and these embodiments are described in the context of the following exemplary system and method.

FIG. 1 illustrates an exemplary block diagram of a system 100 for noisy signal identification from non-stationary audio signals, in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2:
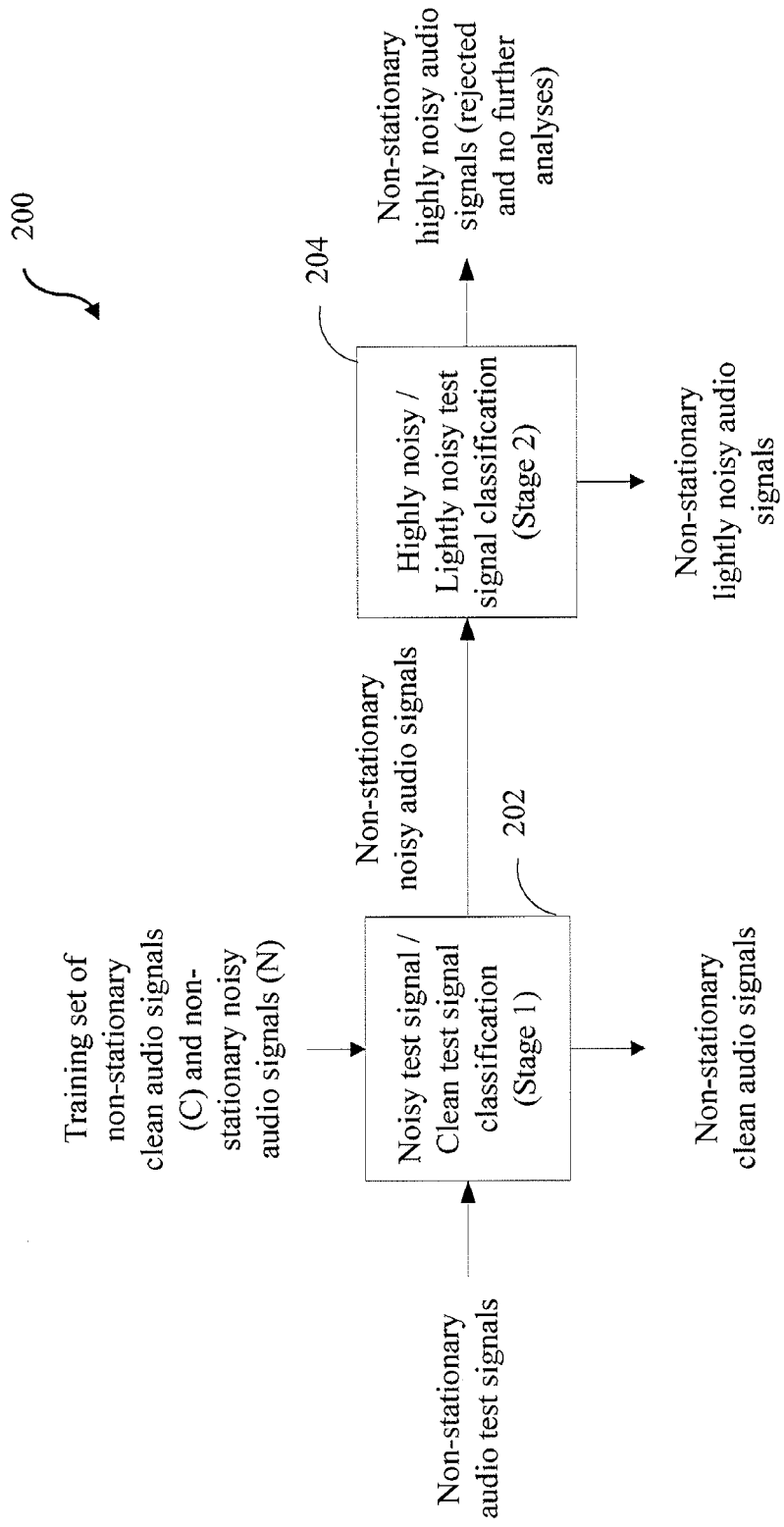
FIG. 2 illustrates an exemplary high level flow chart of a method for noisy signal identification from non-stationary audio signals, in accordance with an embodiment of the present disclosure.

FIG. 2 illustrates an exemplary high level flow chart 200 of a method for noisy signal identification from non-stationary audio signals, in accordance with an embodiment of the present disclosure. In an embodiment, the method of the present disclosure comprises two main stages as illustrated. In stage 1 referenced generally as block 202, non-stationary audio test signals are automatically classified as either non-stationary clean audio signals or non-stationary noisy audio signals. In stage 2 referenced generally as block 204, the non-stationary noisy audio signals are automatically further classified as non-stationary lightly noisy audio signals that may be further analyzed for further information or non-stationary highly noisy audio signals that maybe rejected and not required for further analyses.

Figure 3:
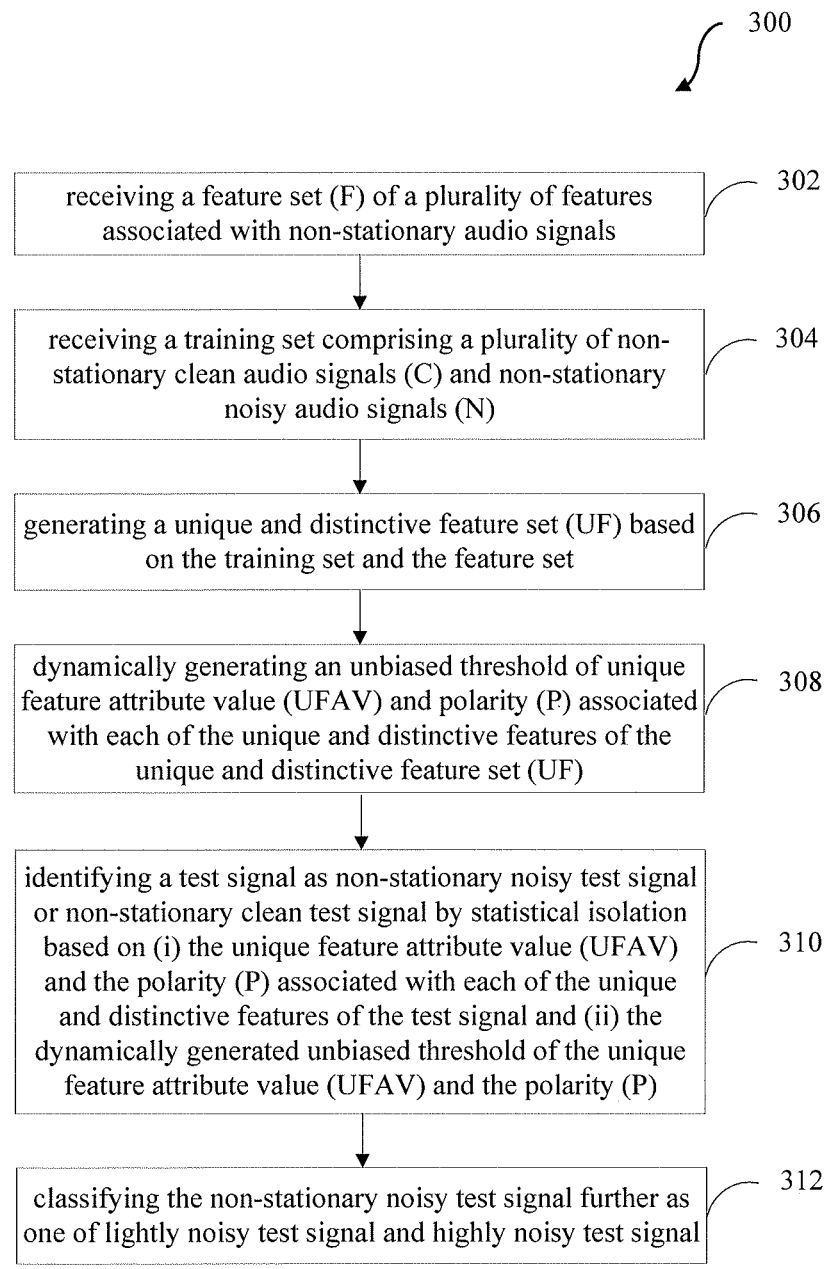
FIG. 3 illustrates an exemplary flow diagram of the method for noisy signal identification from non-stationary audio signals, in accordance with an embodiment of the present disclosure.

FIG. 3 illustrates an exemplary flow diagram of the method 300 for noisy signal identification from non-stationary audio signals, in accordance with an embodiment of the present disclosure, in accordance with an embodiment of the present disclosure. In an embodiment, the system 100 comprises one or more data storage devices or memory 102 operatively coupled to the one or more processors 104 and is configured to store instructions configured for execution of steps of the method 300 by the one or more processors 104. Stage 1 and Stage 2 of FIG. 2 will now be explained in detail with reference to FIG. 3.

In an embodiment, at step 302, the one or more processors 104 of the system 100 are configured to receive a feature set (F) of a plurality of features associated with non-stationary audio signals. In an embodiment, the non-stationary audio signals may be physiological audio signals with a plurality of associated features such as spectral centroid, short-time energy, spectral roll-off, spectral flux, and the like. The feature set (F) may be exhaustive enough to cover all possible features that may be associated with the non-stationary audio signals under consideration for improved performance of the system 100 of the present disclosure.

In an embodiment, at step 304, the one or more processors 104 of the system 100 are configured to receive a training set comprising a plurality of non-stationary clean audio signals (C) and non-stationary noisy audio signals (N).

Figure 4A:
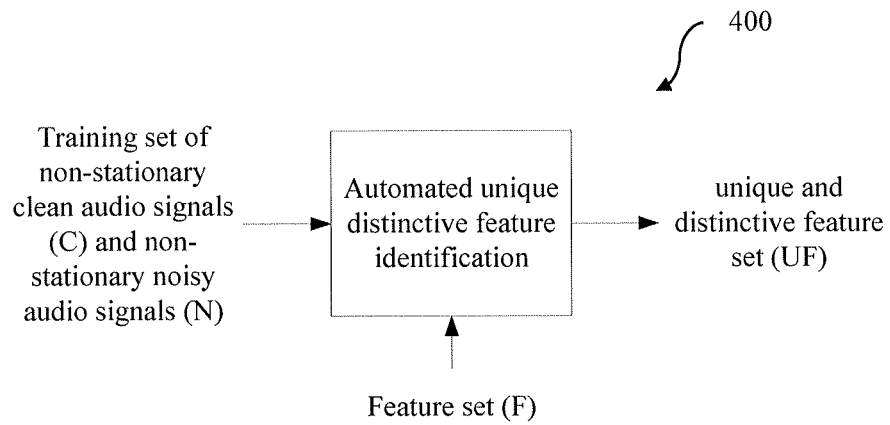
FIG. 4A illustrates a representative block diagram for the step of generating a unique and distinctive feature set based on received training set and feature set, in accordance with an embodiment of the present disclosure.

In an embodiment, at step 306, the one or more processors 104 of the system 100 are configured to generate a unique and distinctive feature set (UF) based on the training set received at step 304 and the feature set received at step 302, as illustrated in FIG. 4A. Firstly, the system 100 extracts feature values for each of the plurality of features associated with the plurality of non-stationary clean audio signals (C) and the non-stationary noisy audio signals (N). Each feature from the feature set (F) is then classified as a unique and distinctive feature of the unique and distinctive feature set (UF) if one of the following conditions are satisfied:

(i) Minimum feature value associated with the non-stationary clean audio signal (C) is greater than maximum feature value associated with the non-stationary noisy audio signal (N) by at least a first pre-determined percentage of the plurality of the non-stationary clean audio signals (C) and at least a second pre-determined percentage of the plurality of the non-stationary noisy audio signals (N).

(ii) Minimum feature value associated with the non-stationary noisy audio signal (N) is greater than maximum feature value associated with the non-stationary clean audio signal (C) by at least the first pre-determined percentage of the plurality of the plurality of non-stationary clean audio signals (C) and at least the second percentage of the plurality of the non-stationary noisy audio signals (N), is satisfied.

In an embodiment, the first pre-determined percentage and the second pre-determined percentage is 90%.

In an exemplary embodiment, say a feature from the feature set (F) is "peak amplitude". Assuming the training set includes 10 clean audio signals (C) and 10 noisy audio signal (N), feature value may be extracted for each of the 10 clean audio signals (C) and 10 noisy audio signals (N). The feature "peak amplitude" may be classified as a unique and distinctive feature of the unique and distinctive feature set (UF) only if one of the following two conditions is satisfied:

(i) minimum value of peak amplitude of the 10 clean audio signals (C) >maximum value of peak amplitude of the 10 noisy audio signals (N) for at least 9 clean audio signals (C) and at least 9 noisy audio signals (N) out of the 10 C and 10 N audio signals in the training set; in this case polarity is +1.

(ii) minimum value of peak amplitude of the 10 noisy audio signals (N) >maximum value of peak amplitude of the 10 clean audio signals (C) for at least 9 clean audio signals (C) and at least 9 noisy audio signals (N) out of the 10 C and 10 N audio signals in the training set; in this case polarity is −1.

From the exemplary embodiment, it may be noted that features that may be classified as unique and distinctive features have associated values close to either a clean class of audio signals or a noisy class of audio signals and can be differentiated in a majority of cases (typically 90%), where cardinality of the unique and distinctive feature set (UF) is less than or equal to cardinality of the feature set (F) i.e. |UF|≤|F|. In another practical example, where the feature set may include features like spectral centroid, short-time energy, spectral roll-off, spectral flux for non-stationary physiological audio signals, the unique and distinctive feature set UF={10% trimmed mean of Fast Fourier Transform (FFT) co-efficients, Skewness of Fast Fourier Transform co-efficients, Frequency below which 80% FFT energy is contained, Kurtosis of Fast Fast Fourier transform co-efficients}.

In accordance with the present disclosure, unique and mutually exclusive features that distinctly differentiate noisy and clean audio signals are automatically generated. Also, the step of generating the unique and distinctive feature set (UF) is independent of any particular classifier.

Figure 4B:
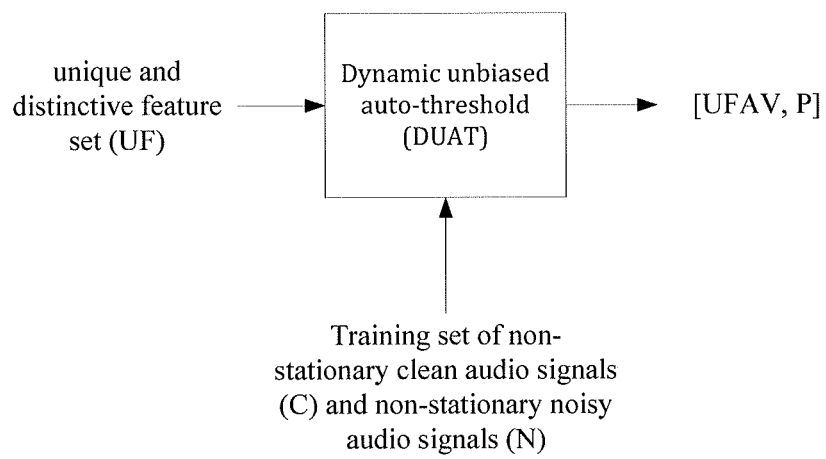
FIG. 4B illustrates a representative block diagram for the step of dynamically generating an unbiased threshold of unique feature attribute value and polarity associated with each of the unique and distinctive features of the unique and distinctive feature set.

In order to differentiate between clean and noisy non-stationary physiological audio signals with respect to the unique and distinctive feature set (UF), at step 308, the one or more processors 104 of the system 100 are configured to dynamically generate an unbiased threshold of unique feature attribute value (UFAV) and polarity (P) associated with each of the unique and distinctive features of the unique and distinctive feature set (UF), as illustrated in FIG. 4B, in an automated manner. The step 308 of the present disclosure ensures that the threshold is automatically and dynamically adjusted if the unique and distinctive feature set (UF) and/or the training set changes.

The dynamically generated unbiased threshold is a tuple consisting of the unique feature attribute value and the polarity, i.e. the Dynamic Unbiased Automatic Threshold DUAT=[unique feature attribute value (UFAV), polarity (P)], where polarity is considered with respect to clean signal and positive polarity (P=1) means the audio signal tends to be clean when the UFAV value of that signal is more than that of DUAT of that UFV. For example, if one of the UFAV is mean of signal amplitude, and UFAV of that feature (mean of signal amplitude) is set at $\varrho$, then P=1 signifies that if signal amplitude of a test signal is more than $\varrho$, the test signal tends to be clean.

In accordance with the present disclosure, the UFAV is equidistant from a majority of non-stationary clean audio signals (C) and the non-stationary noisy audio signals (N) to ensure enhanced accuracy of output of the system 100. In an embodiment, the unique feature attribute value (UFAV) is mean of (i) median of values associated with unique and distinctive features of the plurality of non-stationary clean audio signals and (ii) median of values associated with the unique and distinctive features of the non-stationary noisy audio signals, i.e. $UFAV_n$=mean (median $(UF_{n,\{1,\ldots,(|C+N|)\}})$), $n \in |UF|$, which is the mean of the median of the values associated with unique and distinctive features over the complete training set. It is a point that divides clean and noisy signals with a high probability with respect to that unique feature.

Figure 4C:
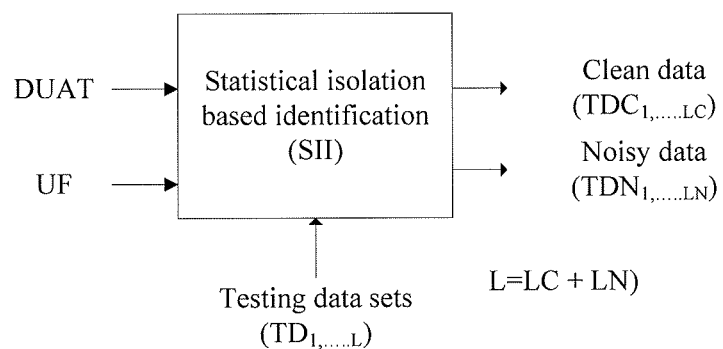
FIG. 4C illustrates a representative block diagram for the step of statistical isolation based identification of a test signal as a noisy test signal or clean test signal.

In an embodiment, at step 310, the one or more processors 104 of the system 100 are configured to identify a test signal as non-stationary noisy test signal or non-stationary clean test signal by statistical isolation based on (i) the unique feature attribute value (UFAV) and the polarity (P) associated with each of the unique and distinctive features of the test signal and (ii) the dynamically generated unbiased threshold of the unique feature attribute value (UFAV) and the polarity (P) as illustrated in FIG. 4C. In an embodiment, the total number of unique and distinctive features are bucketed into clean bucket ($B_C$) and noisy bucket ($B_N$) based on a strict majority voting rule on cardinality of the clean bucket ($B_C$) and cardinality of the noisy bucket ($B_N$). In an embodiment, if the cardinality of the clean bucket ($B_C$) and the cardinality of the noisy bucket ($B_N$) are equal, weighted majority voting rule may be employed wherein clean bucket ($B_C$) may be given more weightage. In order to avert ambiguity, if any, in the decision process, a test signal is identified as clean if $$\text{ceil}\left(\frac{|UF|}{2}\right)$$

number of buckets are from the clean class. Thus, for a test signal, where $|UF|=B_C+B_N$ and $$B_C = \text{ceil}\left(\frac{|UF|}{2}\right) \text{ and } B_N = |UF| - \text{ceil}\left(\frac{|UF|}{2}\right),$$

then that test signal is classified as clean. For instance, if there are 9 unique and distinctive features identified for a test signal which have been bucketed as ($B_C$)=5 and $$(B_N) = 4, \text{ceil}\left(\frac{|9|}{2}\right) = \text{ceil}(4.5) = 5.$$

The test signal may then be identified as a non-stationary clean audio signal.

In an embodiment, Stage 1 of FIG. 2 may comprise steps 302 through 310 as described herein above and Stage 2 of FIG. 2 may comprise step 312 as described herein below with reference to FIG. 3 and FIG. 4A, FIG. 4B and FIG. 4C.

In an embodiment, at step 312, the one or more processors 104 of the system 100 are configured to classify the non-stationary noisy test signal further as one of lightly noisy test signal and highly noisy test signal. The finer lever classification of the non-stationary noisy test signal as lightly noisy test signal is based on one of the following conditions:
(i) Cardinality of the clean bucket (BC) is greater than the cardinality of the unique and distinctive feature set (UF) by a first pre-determined value.
(ii) Euclidian distance between the unique feature attribute value (UFAV) and the values associated with unique and distinctive features of the noisy signal is lesser than the unique feature attribute value (UFAV) by a second pre-determined value in at least a part of the cardinality of the unique and distinctive feature set (UF).

In an embodiment, a noisy test signal may be further classified as lightly noisy if cardinality of the clean bucket ($B_C$) is not less than one third of the cardinality of the unique and distinctive feature set $$(UF) \text{ i.e. } \frac{|UF|}{3} \leq B_C < \text{ceil}\left(\frac{|UF|}{2}\right).$$

In an embodiment, a noisy test signal may be further classified as lightly noisy if Euclidian distance between the unique feature attribute value (UFAV) and the values associated with unique and distinctive features of the noisy signal is not greater than 10% of the unique feature attribute value (UFAV) in at least 50% of the cardinality of the unique and distinctive feature set (UF). For instance, let there be I (=|UF|) number of unique features, and $UF_i=\{E_i\}$, $i \in I$, wherein $E_i$ represents the unique feature attribute value. For each unique feature, the value associated with unique and distinctive features of the noisy test signal is $\Psi_i$ and Euclidian distance $\Theta_i=\|E_i-\Psi_i\|$. If $\Theta_i \leq 0.1 \times E_i$, i∈ceil (½), then that noisy test signal is identified as lightly noisy.

Experimental Data

A method and system of the present disclosure has been tested on on Physionet challenge 2016 datasets and performance is reported as provided herein below:

Non-stationary physiological audio signals from publicly available Phonocardiogram data (https://physionet.org/pn3/challenge/2016/) were used for the experiment.

Data set available: 120 N signals, 3129 C signals

Training set: (N 90 & C 90)

Testing set: (N 30 & C 3039)

This training set consists of five databases (A through E) containing a total of 3,126 heart sound recordings, lasting from 5 seconds to just over 120 seconds.

In this experiment, four features are found to be unique and distinctive features:
1. 10% trimmed mean of the Fourier co-efficients
2. Skewness of the Fourier co-efficients
3. Frequencies below which 80% energy is present.
4. Kurtosis of the Fourier co-efficients.

The corresponding UFAV: [255.05, +1], [0.0003, −1], [32.6, −1], [10.1237, +1].

Based on the method and system of the present disclosure, the aforementioned experiment yielded noise detection with an accuracy of 85.52%.

Conventionally known systems and methods for noisy signal identification from non-stationary audio signals are directed to classifying non-stationary noisy signals into noisy and clean components. Particularly, non-stationary physiological audio signals such as PCG recordings have a lot of noise components which may contain critical information. Automation of conventionally known systems and methods would only result in time saving; further analyses would continue to be restricted to clean components only thereby missing critical information that may have been present in the rejected noisy component. Systems and methods of the present disclosure address this technical problem by facilitating automatic noisy signal identification in a manner that is firstly dynamic and is not dependent on any classifier. It also enables classifying the noisy component further into lightly noisy component that may be taken further for analyses thereby ensuring as much critical information as possible is retrieved from the non-stationary audio signals.

The written description describes the subject matter herein to enable any person skilled in the art to make and use the embodiments of the present disclosure. The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments of the present disclosure may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules comprising the system of the present disclosure and described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The various modules described herein may be implemented as software and/or hardware modules and may be stored in any type of non-transitory computer readable medium or other storage device. Some non-limiting examples of non-transitory computer-readable media include CDs, DVDs, BLU-RAY, flash memory, and hard disk drives.

Further, although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope and spirit of disclosed embodiments being indicated by the following claims.

What is claimed is:

1. A processor implemented method (300) comprising:
receiving a feature set (F) of a plurality of features associated with non-stationary audio signals (302);
receiving a training set comprising a plurality of non-stationary clean audio signals (C) and non-stationary noisy audio signals (N) (304);
generating a unique and distinctive feature set (UF) based on the training set and the feature set (F) (306);

dynamically generating an unbiased threshold of unique feature attribute value (UFAV) and polarity (P) associated with each of the unique and distinctive features of the unique and distinctive feature set (UF) (308);

identifying a test signal as non-stationary noisy test signal or non-stationary clean test signal by statistical isolation based on (i) a unique feature attribute value (UFAV) and polarity (P) associated with the test signal for each of the unique and distinctive features and (ii) the dynamically generated unbiased threshold of the unique feature attribute value (UFAV) and the polarity (P) associated with each of the unique and distinctive features of the unique and distinctive feature set (UF) (310); and classifying the test signal further as one of lightly noisy test signal and highly noisy test signal (312) based on one or more pre-defined conditions when the test signal is identified as the non-stationary noisy test signal.

2. The processor implemented method of claim 1, wherein generating the unique and distinctive feature set (UF) comprises:

extracting feature values from the plurality of non-stationary clean audio signals (C) and the non-stationary noisy audio signals (N) for each of the unique and distinctive features; and classifying each feature from the feature set (F) as a unique distinctive feature of a unique distinctive feature set (UF) if one condition of: (i) a minimum feature value associated with one of the plurality of non-stationary clean audio signals (C) is greater than maximum feature value associated with one of the plurality of non-stationary noisy audio signals (N) by at least a first pre-determined percentage of the plurality of the non-stationary clean audio signals (C) and at least a second pre-determined percentage of the plurality of the non-stationary noisy audio signals (N); and (ii) a minimum feature value associated with one of the plurality of non-stationary noisy audio signals (N) is greater than maximum feature value associated with one of the plurality of non-stationary clean audio signals (C) by at least the first pre-determined percentage of the plurality of the plurality of non-stationary clean audio signals (C) and at least the second percentage of the plurality of the non-stationary noisy audio signals (N), is satisfied.

3. The processor implemented method of claim 2, wherein the first pre-determined percentage and the second pre-determined percentage is 90%.

4. The processor implemented method of claim 1, wherein the unique feature attribute value (UFAV) associated with each of the unique and distinctive features of the unique and distinctive feature set (UF) is a mean of (i) a median of values of the plurality of non-stationary clean audio signals for the unique and distinctive features and (ii) a median of values of the non-stationary noisy audio signals for the unique and distinctive features.

5. The processor implemented method of claim 1, wherein identifying the test signal as non-stationary noisy test signal or non-stationary clean test signal comprises one condition of:

bucketing the unique and distinctive features into a clean bucket ($B_C$) and a noisy bucket ($B_N$) based on a strict majority voting rule on cardinality of the clean bucket ($B_C$) and cardinality of the noisy bucket ($B_N$); and bucketing the unique and distinctive features into a clean bucket ($B_C$) and a noisy bucket ($B_N$) based on a weighted majority voting rule on cardinality of the clean bucket ($B_C$) and cardinality of the noisy bucket ($B_N$).

6. The processor implemented method of claim 5, wherein classifying the non-stationary noisy test signal further as lightly noisy test signal comprises satisfying one condition from the one or more pre-defined conditions including:

cardinality of a clean bucket ($B_C$) is greater than cardinality of the unique and distinctive feature set (UF) by a first pre-determined value, wherein the clean bucket ($B_C$) is one of a) the clean bucket ($B_C$) formed based on the weighted majority voting rule and b) the clean bucket ($B_C$) formed based on the strict majority voting rule; and Euclidian distance between the unique feature attribute value (UFAV) and the values of the non-stationary noisy test signal associated with unique and distinctive features is lesser than the unique feature attribute value (UFAV) associated with each of the unique and distinctive features of the unique and distinctive feature set (UF) by a second pre-determined value in at least a part of the cardinality of the unique and distinctive feature set (UF);

is satisfied.

7. The processor implemented method of claim 6, wherein the cardinality of the clean bucket ($B_C$) is not less than one third of the cardinality of the unique and distinctive feature set (UF).

8. The processor implemented method of claim 6, wherein the Euclidian distance between the unique feature attribute value (UFAV) and the values of the non-stationary noisy test signal associated with unique and distinctive features is not greater than 10% of the unique feature attribute value (UFAV) associated with the unique and distinctive features of the unique and distinctive feature set (UF) in at least 50% of the cardinality of the unique and distinctive feature set (UF).

9. A system (100) comprising:

one or more data storage devices (102) operatively coupled to one or more hardware processors (104) and configured to store instructions configured for execution by the one or more hardware processors to:

receive a feature set (F) of a plurality of features associated with non-stationary audio signals;

receive a training set comprising a plurality of non-stationary clean audio signals (C) and non-stationary noisy audio signals (N);

generate a unique and distinctive feature set (UF) based on the training set and the feature set (F);

dynamically generate an unbiased threshold of unique feature attribute value (UFAV) and polarity (P) associated with each of the unique and distinctive features of the unique and distinctive feature set (UF);

identify a test signal as non-stationary noisy test signal or non-stationary clean test signal by statistical isolation based on (i) a unique feature attribute value (UFAV) and polarity (P) associated with the test signal for each of the unique and distinctive features and (ii) the dynamically generated unbiased threshold of the unique feature attribute value (UFAV) and the polarity (P) associated with each of the unique and distinctive features of the unique and distinctive feature set (UF); and classify the test signal further as one of lightly noisy test signal and highly noisy test signal based on one or more pre-defined conditions when the test signal is identified as the non-stationary noisy test signal.

10. The system of claim 9, wherein the one or more hardware processors are further configured to generate the unique and distinctive feature set (UF) by:
 extracting feature values from the plurality of non-stationary clean audio signals (C) and the non-stationary noisy audio signals (N) for each of the unique and distinctive features; and
 classifying each feature from the feature set (F) as a unique distinctive feature of a unique distinctive feature set (UF) if one condition of: (i) a minimum feature value associated with one of the plurality of non-stationary clean audio signals (C) is greater than maximum feature value associated with one of the plurality of non-stationary noisy audio signals (N) by at least a first pre-determined percentage of the plurality of the non-stationary clean audio signals (C) and at least a second pre-determined percentage of the plurality of the non-stationary noisy audio signals (N); and (ii) a minimum feature value associated with one of the plurality of non-stationary noisy audio signals (N) is greater than maximum feature value associated with one of the plurality of non-stationary clean audio signals (C) by at least the first pre-determined percentage of the plurality of the plurality of non-stationary clean audio signals (C) and at least the second percentage of the plurality of the non-stationary noisy audio signals (N), is satisfied.

11. The system of claim 10, wherein the first pre-determined percentage and the second pre-determined percentage is 90%.

12. The system of claim 9, wherein the unique feature attribute value (UFAV) associated with each of the unique and distinctive features of the unique and distinctive feature set (UF) is a mean of (i) a median of values of the plurality of non-stationary clean audio signals for the unique and distinctive features and (ii) a median of values of the non-stationary noisy audio signals for the unique and distinctive features.

13. The system of claim 9, wherein the one or more hardware processors are further configured to identify the test signal as non-stationary noisy test signal or non-stationary clean test signal if one condition of:
 bucketing the unique and distinctive features into a clean bucket ($B_C$) and a noisy bucket ($B_N$) based on a strict majority voting rule on cardinality of the clean bucket ($B_C$) and cardinality of the noisy bucket ($B_N$); and
 bucketing the unique and distinctive features into a clean bucket ($B_C$) and a noisy bucket ($B_N$) based on a weighted majority voting rule on cardinality of the clean bucket ($B_C$) and cardinality of the noisy bucket ($B_N$); is satisfied.

14. The system of claim 13, wherein the one or more hardware processors are further configured to classify the non-stationary noisy test signal further as lightly noisy test signal if one condition from the one or more pre-defined conditions including:
 cardinality of a clean bucket ($B_C$) is greater than cardinality of the unique and distinctive feature set (UF) by a first pre-determined value, wherein the clean bucket ($B_C$) is one of a) the clean bucket ($B_c$) formed based on the weighted majority voting rule and b) the clean bucket ($B_C$) formed based on the strict majority voting rule; and
 Euclidian distance between the unique feature attribute value (UFAV) and the values of the non-stationary noisy test signal associated with unique and distinctive features is lesser than the unique feature attribute value (UFAV) associated with each of the unique and distinctive features of the unique and distinctive feature set (UF) by a second pre-determined value in at least a part of the cardinality of the unique and distinctive feature set (UF);
 is satisfied.

15. The system of claim 14, wherein the cardinality of the clean bucket ($B_C$) is not less than one third of the cardinality of the unique and distinctive feature set (UF).

16. The system of claim 14, wherein the Euclidian distance between the unique feature attribute value (UFAV) and the values of the non-stationary noisy test signal associated with unique and distinctive features is not greater than 10% of the unique feature attribute value (UFAV) associated with the unique and distinctive features of the unique and distinctive feature set (UF) in at least 50% of the cardinality of the unique and distinctive feature set (UF).

17. A computer program product comprising a non-transitory computer readable medium having a computer readable program embodied therein, wherein the computer readable program, when executed on a computing device, causes the computing device to:
 receive a feature set (F) of a plurality of features associated with non-stationary audio signals;
 receive a training set comprising a plurality of non-stationary clean audio signals (C) and non-stationary noisy audio signals (N);
 generate a unique and distinctive feature set (UF) based on the training set and the feature set (F);
 dynamically generate an unbiased threshold of unique feature attribute value (UFAV) and polarity (P) associated with each of the unique and distinctive features of the unique and distinctive feature set (UF);
 identifying a test signal as non-stationary noisy test signal or non-stationary clean test signal by statistical isolation based on (i) a unique feature attribute value (UFAV) and polarity (P) associated with the test signal for each of the unique and distinctive features and (ii) the dynamically generated unbiased threshold of the unique feature attribute value (UFAV) and the polarity (P) associated with each of the unique and distinctive features of the unique and distinctive feature set (UF); and
 classifying the test signal further as one of lightly noisy test signal and highly noisy test signal based on one or more pre-defined conditions when the test signal is identified as the non-stationary noisy test signal.

* * * * *